United States Patent
Weeber et al.

(10) Patent No.: US 9,724,190 B2
(45) Date of Patent: Aug. 8, 2017

(54) CUSTOMIZED MULTIFOCAL OPHTHALMIC LENS

(75) Inventors: Henk A. Weeber, Groningen (NL); Patricia A. Piers, Groningen (NL); Marrie H. Van der Mooren, Engelbert (NL)

(73) Assignee: AMO Groningen B.V., Groningen (NL)

( * ) Notice: Subject to any disclaimer, the term of this patent is extended or adjusted under 35 U.S.C. 154(b) by 1792 days.

(21) Appl. No.: 12/815,157

(22) Filed: Jun. 14, 2010

(65) Prior Publication Data

US 2010/0281021 A1 Nov. 4, 2010

(51) Int. Cl.
*A61F 2/16* (2006.01)
*A61B 18/20* (2006.01)

(52) U.S. Cl.
CPC ...... *A61F 2/1618* (2013.01); *A61F 2240/002* (2013.01)

(58) Field of Classification Search
CPC ......... G06F 17/30864; G06F 17/30867; G06F 17/3089; A61F 2/16; A61F 2/1613; A61F 2/1616; A61F 2/1618; A61F 2/1621; A61F 2/1648; A61F 2/1654; A61F 9/008; A61F 9/00802; A61F 9/00812; A61F 2009/00812; A61F 2009/00885; A61F 2009/00887; A61F 2009/00895
USPC ...... 707/790; 623/4.1, 5.11–5.13, 6.11, 6.12, 623/6.23, 6.24; 604/4–6, 10–12; 128/898
See application file for complete search history.

(56) References Cited

U.S. PATENT DOCUMENTS

| | | |
|---|---|---|
| 4,881,804 A | 11/1989 | Cohen |
| 5,144,483 A | 9/1992 | Cohen |
| 5,150,137 A | 9/1992 | Owens, II et al. |
| 5,225,858 A | 7/1993 | Portney |
| 5,699,142 A | 12/1997 | Lee et al. |
| 5,903,334 A | 5/1999 | Sakurai et al. |
| 6,199,983 B1 | 3/2001 | Kato et al. |
| 6,499,843 B1 | 12/2002 | Cox et al. |
| 6,527,389 B2 | 3/2003 | Portney |

(Continued)

FOREIGN PATENT DOCUMENTS

| | | |
|---|---|---|
| EP | 0061918 B1 | 9/1985 |
| EP | 1637101 A1 | 3/2006 |

(Continued)

OTHER PUBLICATIONS

1-Save-On-Lens Contacts, Cosmetic Contact Lens, Retrieved from the Internet: http://www.1-save-on-lens.com/corporate.html, Retrieved dated Mar. 3, 2017, 10 pages.

(Continued)

*Primary Examiner* — Ahmed Farah
(74) *Attorney, Agent, or Firm* — Abbott Medical Optics Inc.

(57) ABSTRACT

System and method for customizing multifocal ophthalmic lenses, such as an intraocular lens (IOL) or the like, that may be tailored for an individual patient or group of patients beyond the selection of a particular IOL power. One or more eye factors of the patient are determined, a set of different multifocal intraocular lenses having a similar base power are determined based on the eye factors, and a multifocal intraocular lens is selected for the patient from the set based on the eye factors.

26 Claims, 5 Drawing Sheets

(56) References Cited

U.S. PATENT DOCUMENTS

| | | | |
|---|---|---|---|
| 6,557,998 B2 | 5/2003 | Portney | |
| 6,609,793 B2 | 8/2003 | Norrby et al. | |
| 7,261,412 B2 | 8/2007 | Somani et al. | |
| 7,780,293 B2 | 8/2010 | Andino et al. | |
| 7,980,697 B2 | 7/2011 | Tsukada et al. | |
| 8,109,631 B2 | 2/2012 | Guilloux et al. | |
| 8,444,267 B2* | 5/2013 | Weeber | A61F 2/1618 351/159.35 |
| 2002/0193704 A1 | 12/2002 | Goldstein et al. | |
| 2003/0007123 A1 | 1/2003 | Broderick et al. | |
| 2003/0214628 A1* | 11/2003 | Patel | 351/200 |
| 2004/0004633 A1 | 1/2004 | Perry et al. | |
| 2004/0027679 A1 | 2/2004 | Welk et al. | |
| 2004/0046287 A1 | 3/2004 | Andino et al. | |
| 2004/0054358 A1 | 3/2004 | Cox | |
| 2004/0085515 A1 | 5/2004 | Roffman et al. | |
| 2004/0119174 A1 | 6/2004 | Hofmann et al. | |
| 2004/0156013 A1 | 8/2004 | Lindacher et al. | |
| 2004/0156014 A1 | 8/2004 | Piers et al. | |
| 2004/0169820 A1 | 9/2004 | Dai et al. | |
| 2004/0193054 A1 | 9/2004 | Leblanc et al. | |
| 2004/0246440 A1 | 12/2004 | Andino et al. | |
| 2004/0249729 A1 | 12/2004 | Matsumura et al. | |
| 2005/0088616 A1 | 4/2005 | Nason et al. | |
| 2005/0122472 A1 | 6/2005 | Fisher et al. | |
| 2005/0157254 A1 | 7/2005 | Shinohara et al. | |
| 2005/0270482 A1 | 12/2005 | Fisher et al. | |
| 2006/0023162 A1* | 2/2006 | Azar et al. | 351/246 |
| 2006/0064326 A1 | 3/2006 | Tucker | |
| 2006/0098162 A1* | 5/2006 | Bandhauer et al. | 351/159 |
| 2006/0100704 A1 | 5/2006 | Blake et al. | |
| 2007/0161972 A1 | 7/2007 | Felberg et al. | |
| 2007/0296915 A1 | 12/2007 | Legerton et al. | |
| 2008/0004698 A1 | 1/2008 | Das et al. | |
| 2008/0033546 A1* | 2/2008 | Liang | A61F 2/147 623/5.11 |
| 2008/0033836 A1 | 2/2008 | Shinohara et al. | |
| 2008/0198328 A1 | 8/2008 | Seriani et al. | |
| 2008/0212024 A1 | 9/2008 | Lai | |
| 2009/0161071 A1 | 6/2009 | Dreher et al. | |
| 2009/0174865 A1 | 7/2009 | Privitera et al. | |
| 2009/0219486 A1 | 9/2009 | Bonnin et al. | |
| 2009/0250828 A1 | 10/2009 | Rosen et al. | |
| 2009/0290125 A1 | 11/2009 | Varnas et al. | |
| 2010/0134760 A1 | 6/2010 | Salvati et al. | |
| 2010/0238404 A1 | 9/2010 | Newman et al. | |
| 2010/0281021 A1 | 11/2010 | Weeber et al. | |
| 2010/0296048 A1 | 11/2010 | Weatherby | |
| 2010/0296053 A1 | 11/2010 | Marin et al. | |
| 2010/0296058 A1 | 11/2010 | Ho et al. | |
| 2010/0314440 A1 | 12/2010 | Maloney | |
| 2011/0043754 A1 | 2/2011 | Hatanaka | |
| 2011/0157545 A1 | 6/2011 | Applegate et al. | |
| 2011/0184757 A1 | 7/2011 | Daniel | |
| 2011/0270596 A1 | 11/2011 | Weeber | |
| 2011/0273666 A1 | 11/2011 | Warden et al. | |
| 2012/0011565 A1 | 1/2012 | Garlie et al. | |
| 2012/0147324 A1 | 6/2012 | Marin et al. | |
| 2012/0271413 A1* | 10/2012 | Dai | A61B 3/0025 623/6.27 |

FOREIGN PATENT DOCUMENTS

| | | |
|---|---|---|
| EP | 2229091 B1 | 8/2016 |
| JP | H05154108 A | 6/1993 |
| JP | 2004287626 A | 10/2004 |
| JP | 2005131249 A | 5/2005 |
| JP | 4795549 B2 | 10/2011 |
| WO | 2005116890 A1 | 12/2005 |
| WO | 2006020422 A1 | 2/2006 |
| WO | WO2006053216 A2 | 5/2006 |
| WO | 2008131362 A2 | 10/2008 |
| WO | 2010009450 A1 | 1/2010 |
| WO | 2011115119 A1 | 9/2011 |

OTHER PUBLICATIONS

LA sight: Lifestyle Lens Implants, Retrieved from the Internet: http://www.la-sight.com/cataract-surgery/lifestyle-lens-implants, Retrieved dated Mar. 3, 2017, 6 pages.

Lens Design, Copyright: 2003-2011.

Mason I., et al., "Managing Patient Records in the Eye Unit," Community Eye Health Journal, Dec. 2010, vol. 23 (74), pp. 46-47.

Sheehan M.T., Thesis: Eye Modelling for Personalised Intraocular Lens Design, National University of Ireland Galway, Aug. 2012, 255 pages.

The Active Lifestyle IOL, http://www.lenstec.com/products/tetraflex/overview/, copyright 2010, retrieved from the wayback machine (https://archive.org/web/) on Jun. 3, 2017.

Warren Eye Care: Customized Contact Lenses, Retrieved from the Internet: http://www.warreneyecarecenter.com/ better-vision-correction/customized-contact-lenses.html, Retrieved dated Mar. 3, 2017, 2 pages.

Zeiss: Innovative Intraocular Lenses the New Dimension of Vision, dated Mar. 20, 2008, 11 pages.

Zeiss: IOLMaster with Software Version V 3.0, Date of Creation of Document—Dec. 3, 2001, 5 pages.

* cited by examiner

CUSTOMIZED MULTIFOCAL OPHTHALMIC LENS

CROSS-REFERENCE TO RELATED APPLICATIONS

This application is a National Phase Patent Application and claims priority to and the benefit of PCT/US2008/086827, filed on Dec. 15, 2008, which claims the benefit of U.S. Provisional Application No. 61/007,809, filed Dec. 13, 2007.

BACKGROUND OF THE INVENTION

Field of the Invention

This invention generally relates to optical correction, and in exemplary embodiments provides methods, devices, and systems for mitigating or treating defects of the eye. Among the exemplary embodiments, the invention may provide multifocal intraocular lenses.

Background

Presbyopia is a condition that affects the accommodation properties of the eye. As objects move closer to a young, properly functioning eye, the effects of ciliary muscle contraction and zonular relaxation allow the lens of the eye to become rounder or more convex, and thus increase the optical power and ability of the eye to focus at near distances. Accommodation can allow the eye to focus and refocus between near and far objects.

Presbyopia typically develops as a person ages, and is associated with a natural progressive loss of accommodation. A presbyopic eye often loses the ability to rapidly and easily refocus on objects at varying distances. The ability to focus on objects at near distances may also diminish with the presbyopic eye. Although this condition progresses over the lifetime of an individual, the effects of presbyopia usually become noticeable after the age of 45 years. By the age of 65 years, the crystalline lens has often lost almost all elastic properties and has only a limited ability to change shape, or residual accommodation. Residual accommodation refers to the amount of accommodation that remains in the eye. A lower degree of residual accommodation contributes to more severe presbyopia, whereas a higher amount of residual accommodation correlates with less severe presbyopia.

Along with reductions in accommodation of the eye, age may also induce clouding of the lens due to the formation of cataracts. Cataracts may form in the hard central nucleus of the lens, in the softer peripheral cortical portion of the lens, or at the back of the lens. Cataracts can be treated by the replacement of the cloudy natural lens with an artificial lens. Phacoemulsification systems often use ultrasound energy to fragment the natural lens and aspirate the lens material from the eye. An artificial lens replaces the natural lens in the eye, with the artificial lens often being referred to as an intraocular lens (IOL).

After replacement of the natural lens with an intraocular lens, patients may have little or no ability to adjust the optical power associated with the optical tissues of the eye so as to maintain visual quality when changing viewing distance (for example, between viewing a far object while driving and viewing a near object while reading small print). Fortunately, a variety of technologies have been developed that enhance the ability of IOLs to facilitate viewing objects at different distances. Multifocal IOLs may, for example, rely on a diffractive optical surface to direct portions of the light energy toward differing focal distances, thereby allowing the patient to see both near and far objects.

While generally successful at mitigating presbyopia, as with all successes, still more improvements would be desirable. With existing multifocal IOLs, the performance and patient satisfaction may depend on several aspects related to the individual patient. As a result, not all patients are satisfied with multifocal IOLs after implantation for a variety of reasons.

In light of the above, it would be desirable to provide improved IOLs for cataract patients and others. IOL lens design may include a compromise among various design objectives. It would be particularly beneficial if these improved IOLs could take advantage of the capabilities of diffractive multifocal optics, and would enhance patient satisfaction by having optical attributes that are more tailored to the needs and desires of the patient.

SUMMARY OF THE INVENTION

The present invention generally provides improved optical devices, systems, and methods, with exemplary embodiments providing improved ophthalmic lenses. Customized multifocal ophthalmic lenses, such as intraocular lenses (IOLs) and the like, may be tailored or selected for an individual patient or group of patients, rather than limiting the selection of the multifocal ophthalmic lens to a particular IOL power (e.g., a one-size-fits-all multifocal attempt at mitigation of presbyopia for a wide variety of patients using a single IOL structure).

In one embodiment, a system for producing a custom intraocular lens for a patient is provided. The system includes a memory and a processor coupled to the memory. The memory is configured to store a first database of lifestyle parameters, a second database of eye factors, and a third database of multifocal intraocular lenses. The processor is configured to determine an add power based on the first database and the second database and select the custom intraocular lens from the third database based on the add power.

In another embodiment, a system is provided for producing a custom multifocal intraocular lens having a diffractive surface with one or more echelettes. The system includes a memory and a processor coupled to the memory. The memory is configured to store a first database of lifestyle parameters and a second database of eye factors. The processor is configured to determine at least one characteristic of the one or more echelettes based on the first database and the second database and select a diffractive multifocal intraocular lens based on the at least one characteristic.

In another embodiment, a method of producing a multifocal intraocular lens for a patient is provided including determining one or more eye factors of the patient, determining a set of different multifocal intraocular lenses based on the one or more eye factors of the patient, and selecting the multifocal intraocular lens for the patient from the set of multifocal intraocular lenses based on the one or more eye factors of the patient. The multifocal intraocular lenses of the set of multifocal intraocular lenses have a similar base power.

BRIEF DESCRIPTION OF THE DRAWINGS

In the drawings, wherein like reference numerals refer to similar components.

DETAILED DESCRIPTION

The present invention generally provides improved ophthalmic devices, systems, and methods. In exemplary embodiments, the invention provides multifocal ophthalmic lenses (e.g., intraocular lenses (IOLs) and the like) that employ refractive and/or diffractive techniques, and that are customized for a particular patient or patient population subgroup. Rather than being limited to selection of a particular IOL power (which typically represents a one-size-fits-all multifocal attempt at presbyopia mitigation for a wide variety of patients using a single IOL structure), the multifocal lens design is tailored or selected for an individual patient or group of patients. For example, a multifocal intraocular lens may be selected for the patient from among a set of appropriate multifocal intraocular lenses based on one or more patient parameters. As part of determining the appropriate multifocal intraocular lenses for the set, one or more IOL parameters/characteristics may be selected for emphasis or weighting based on the patient parameter(s).

Some examples of patient parameters that may be considered during selection, design, and/or fabrication of the custom multifocal IOLs described herein include, but are not necessarily limited to: estimated post-operative pupil size or sizes, optionally under different viewing conditions including differing lighting conditions (e.g., photopic, mesopic, or the like) and/or differing viewing distances (e.g., near, far, or the like); age; cataract grade; lifestyle assessment of the patient's vision needs (such as based on a questionnaire, physician assessment, or the like); shape of the cornea; length of the eye; anterior chamber depth; historic refraction; medical status of the retina; any combinations thereof; and the like.

Some IOL parameters that may be changed (or that may differ among selectable alternative IOLs) or emphasized for different patients include, but are not necessarily limited to: aberration correction; add power(s) for far, near, and/or intermediate focus; depth of focus of one or more focal points; intermediate vision; spectral light transmission characteristics (e.g., violet, blue, ultraviolet (UV) blockers, or the like); pupil dependent characteristics (such as a central zone size, one or more of the foregoing parameters as based on the pupil, or the like); and/or other parameters.

Figure 1:
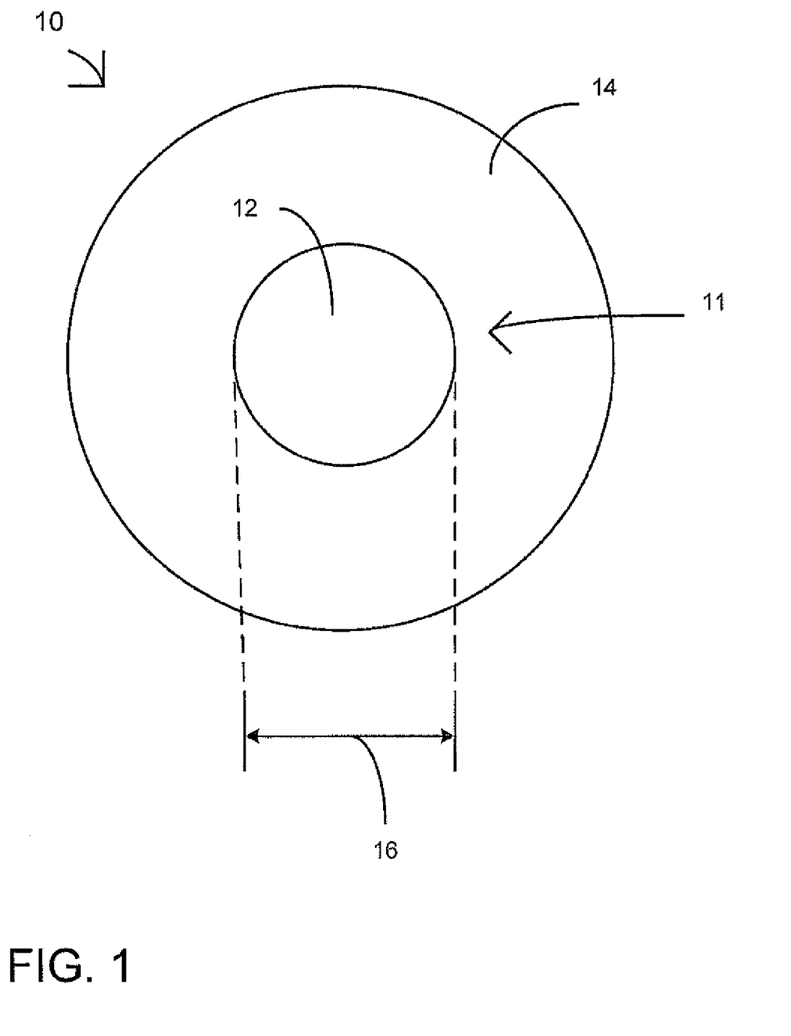
FIG. 1 schematically illustrates an exemplary embodiment of an intraocular lens incorporating aspects of the present invention.

A variety of multifocal intraocular lenses employing refractive and/or diffractive techniques can be customized for a particular patient or patient population subgroup and/or utilized for selective population of a group or database of lenses particularly suited for the patient or patient population subgroup. An exemplary customized intraocular lens for a particular patient may, for example, comprise a pupil-dependent bifocal diffractive intraocular lens 10, as schematically illustrated in FIG. 1. The lens 10 has a central portion 11 that includes a bifocal diffractive structure 12 producing a 50:50 split of the incoming light energy, with about an even distribution between the light energy being directed to a first focal length and the light energy being directed to a different focal length. Examples of diffractive IOL structures are described, for example, in U.S. Pat. No. 5,144,483, and in U.S. Pat. No. 4,881,804, and examples of refractive multifocal intraocular lenses are described in U.S. Pat. Nos. 6,527,389; 5,225,858; and 6,557,998. Each of these references is incorporated herein by reference, and some embodiments may employ one or more structures similar to (or derived from) those described by U.S. Pat. Nos. 4,881,804; 5,144,483; 6,527,389; 5,225,858; and 6,557,998. Other multifocal intraocular lenses having refractive and/or diffractive elements may also be used for customization or selection to populate a desired group of lenses (e.g., meeting predetermined criteria for the particular patient).

A peripheral portion 14 of the lens 10 may include a monofocal structure that directs substantially all of the light incident thereon to a single focal length. In one embodiment, the differing focal lengths of the central portion 12 include a near focus and a far focus, and the monofocal peripheral portion 14 directs light to the far focus. The diameter of the central portion 12 is in a range from about 1 mm to about 6 mm.

As the eye adjusts to different viewing conditions (including both different levels of lighting and different viewing distances), the pupil of the eye often varies in size. Different patients have different pupil sizes. Additionally, the constriction or change in pupil size of patients typically varies, so that two patients that have the same pupil size when viewing the same distant objects under low light conditions may have differing pupil sizes when viewing the same near objects under bright light.

In an exemplary embodiment, the central portion 12 has a size, such as a diameter 16, that is tuned to maximize the performance of the lens 10 for an individual patient or group of patients based at least in part on the patient pupil size. A lens having a smaller central portion may be selected for patients having smaller pupils, and a lens having a larger central portion may be selected for patients having larger pupils.

In the exemplary embodiment of the lens 10, a specific lens design may be chosen based on estimated post-operative pupil sizes. Pupil sizes for the patient post-procedure (such as IOL insertion and/or cataract removal) can be estimated based on preoperative pupil sizes, patient age, the grade of cataract, the type of surgical procedure that is planned, and other factors. Empirical studies in which measurements of pupils are taken before and after surgery for patients of different ages, grade of cataracts, and the like, may be employed. Alternative embodiments may employ lens types that can be adjusted post-operatively, such as structures analogous to or derived from a Calhoun lens. When using such structures, the post-operative pupil size can be measured and the lens adjusted accordingly.

Figure 5:
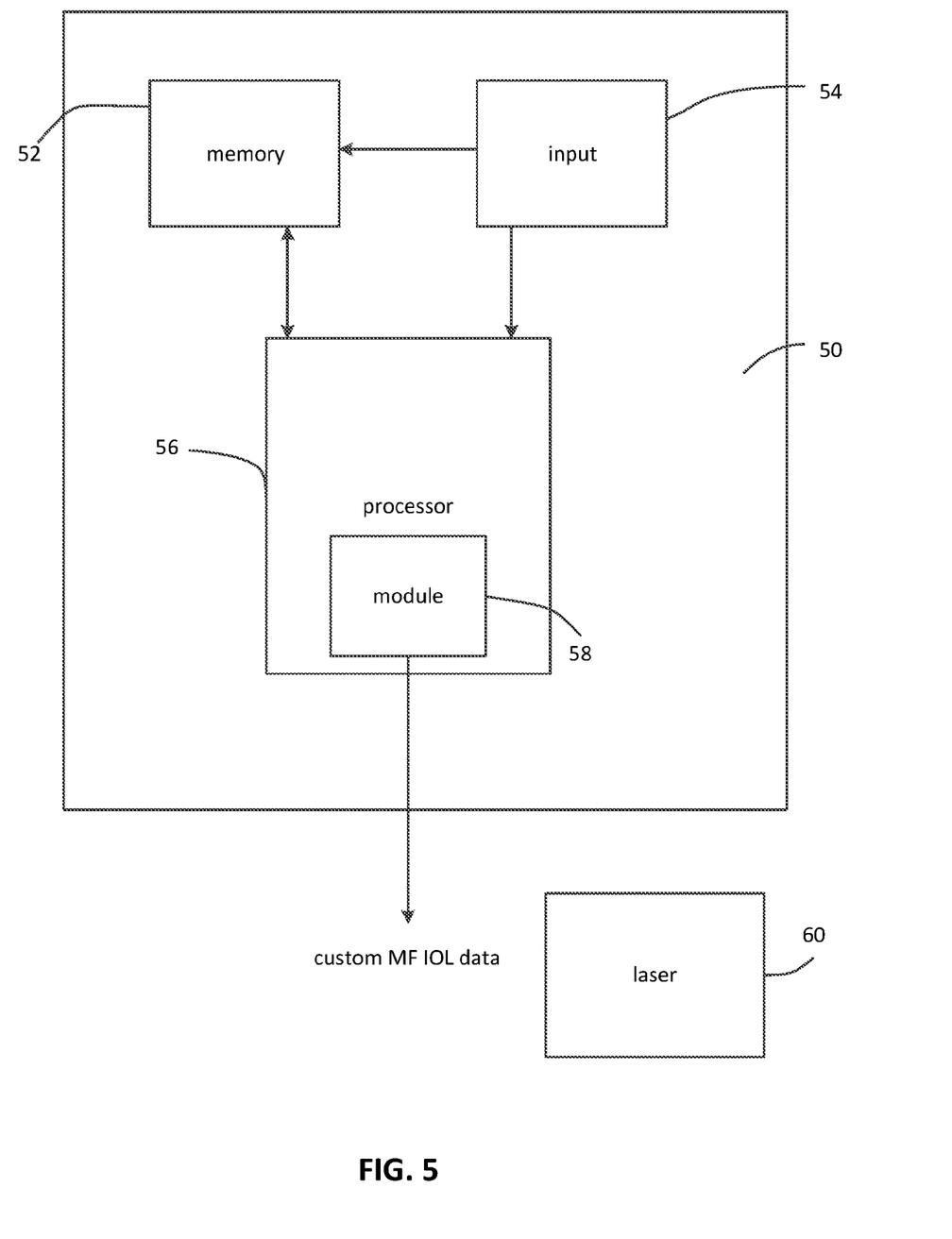
FIG. 5 illustrates a block diagram of an exemplary embodiment of a system for customizing a multifocal lens and of a laser.

Alternative embodiments may be designed specifically to allow or enhance postoperative ophthalmic treatments, such as laser assisted refractive surgery as may be performed by a laser 60 shown in FIG. 5, or to effect a desired optical outcome in combination with additional ophthalmic lenses (e.g., eyeglasses, contact lenses, intracorneal implants or inserts, and the like). For example, laser assisted refractive surgery may be used to fine-tune the refraction or to extend the depth of focus. Combinations with additional ophthalmic lenses may comprise the use of corneal inlays, contact lenses, or spectacles, in order to fine-tune the optical characteristics, or to alter the image magnification on the retina.

Regarding the interaction between pupil sizes under different viewing conditions and the size of the central portion so as to mitigate presbyopia, analogous approaches for presbyopia correction using patient data are described in U.S. Pat. Publication No. 2004/0169820 in the name Dai et al., the full disclosure of which is incorporated herein by reference. For example, a prescription may be established that mitigates or treats presbyopia for the particular patient, and the shape of the multifocal intraocular lens may be designed or selected to correspond to the optical shape associated with this prescription. Some embodiments of the lens 10 may have optical or other characteristics as described in U.S. Pat. Publication No. 2004/0169820, although other embodiments omit the same. For example, some embodiments of the lens 10 may have optical or other characteristics associated with one or more of the ablation shapes for mitigating presbyopia described in U.S. Pat. Publication No. 2004/0169820.

Note that the lens 10 need not necessarily be limited to a bifocal lens embodiment. Other embodiments that may employ aspects of the present invention include trifocal lenses, aspheric lenses, and the like. For example, aspheric IOLs are described in U.S. Pat. No. 6,609,793 in the name of Norrby et al., in U.S. Pat. Publication No. 2004/0156014 in the name of Piers et al., and in other references. Both of the above-referenced applications are incorporated herein by reference. Related approaches for mitigation and/or correction of presbyopia using patient data may also employ multifocal apodization, such as described in U.S. Pat. No. 5,699,142, in the name of Lee et al. (also incorporated herein by reference), as well as other apodized multifocal approaches.

Techniques and approaches developed for contact lenses may also be employed in some aspects of the present invention. For example, the design of the contact lens characteristics described in U.S. Pat. Publication No. 2004/0085515, the disclosure of which is incorporated herein by reference, may be employed to customize the optical characteristics of the multifocal intraocular lens for the patient.

Some embodiments may benefit by using lower add power in the central portion 11. Lowering add power can result in an increased (e.g., farther) reading distance and improved viewing of intermediately positioned objects. The modulation transfer function (MTF) may be somewhat lower, and less halo and scatter can occur when the add power is limited to less than 3 D, the add power often being less than 2.5 D and optionally being 2 D or less.

Figure 2:
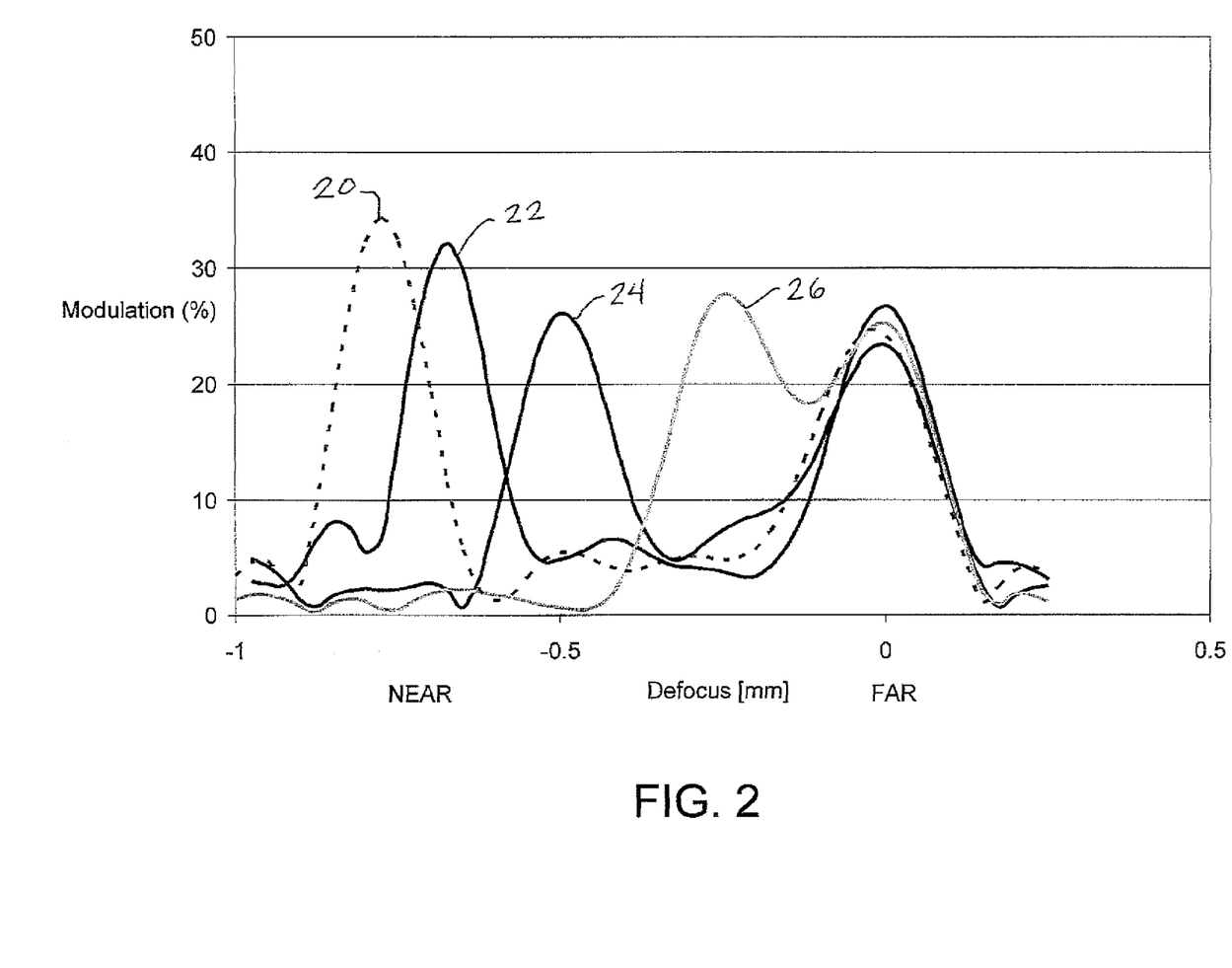
FIGS. 2-3 graphically illustrate optical performance, at differing viewing distances, of multifocal diffractive intraocular lenses having differing characteristics that may be suitable for differing patients.
Figure 3:
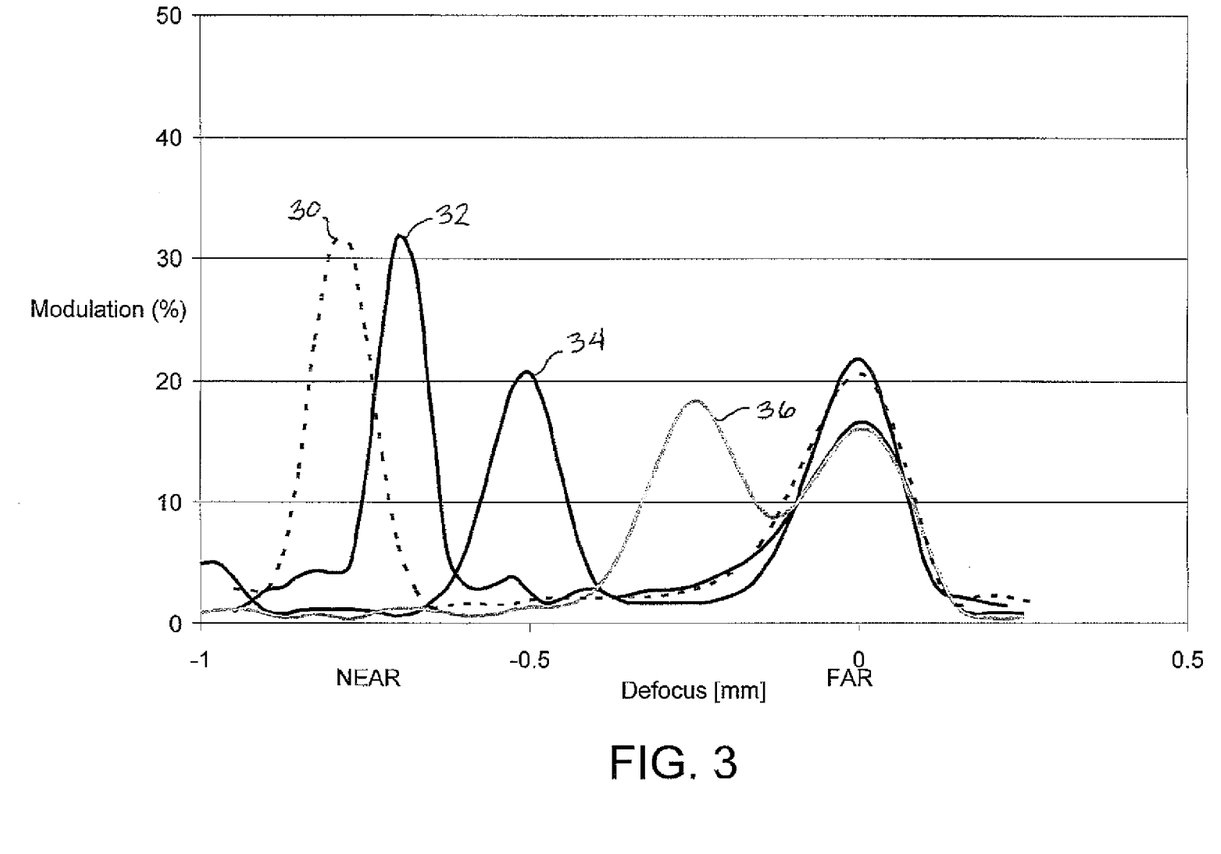

Referring to FIGS. 2 and 3, optical performance, at differing viewing distances, of different multifocal diffractive intraocular lenses are graphically illustrated. Each of these intraocular lenses have characteristics that may be suitable for different patients. FIG. 2 is a through-focus plot of modulation transfer functions (MTFs) 20, 22, 24, 26 at 50 line pairs per mm (or, equivalently, cycles per mm or c/mm) for different multifocal diffractive IOLs at a first pupil size (e.g., about 3 mm). This pupil size may correspond with a normal viewing condition. A first MTF 20 is associated with a diffractive multifocal IOL without add power. A second MTF 22 is associated with a diffractive multifocal IOL with about 3.5 D of add power. A third MTF 24 is associated with a diffractive multifocal IOL with about 2 D of add power. A fourth MTF 26 is associated with a diffractive multifocal IOL with about 1 D of add power. The fourth MTF 26 associated (with the relatively lower add power) indicates a region of extended depth of focus, in comparison with the other MTFs 20, 22, 24.

FIG. 3 is a through-focus plot of modulation transfer functions (MTFs) 30, 32, 34, 36 for different multifocal diffractive IOLs at a second pupil size (e.g., about 5 mm). In contrast with the first pupil size (associated with the MTFs 20, 22, 24, 26 shown in FIG. 2), this pupil size may correspond with a lower lighting viewing condition compared with the normal viewing condition. A first MTF 30 is associated with a diffractive multifocal IOL without add power. A second MTF 32 is associated with a diffractive multifocal IOL with about 3.5 D of add power. A third MTF 34 is associated with a diffractive multifocal IOL with about 2 D of add power. A fourth MTF 36 is associated with a diffractive multifocal IOL with about 1 D of add power. The fourth MTF 36 (with the relatively lower add power) indicates a region of extended depth of focus, in comparison with the other MTFs 30, 32, 34, under lower lighting viewing conditions.

As best shown in FIGS. 2 and 3, each of the corresponding multifocal diffractive IOLs have different properties corresponding with different optical performances. A variety of structural elements may be used to produce the desired multifocal diffractive IOL. For example, a diffractive pattern with a relatively low add power may be imposed on one shape to define the overall form of a posterior surface of the optic. The preceding embodiments are merely for illustrative purposes, and should not be construed as limiting in any way. The parameters of the multifocal diffractive IOL may also be adjusted to suit a particular set of design objectives or to reflect a particular set of measurements for a particular set of eyes or an individual eye. For example, the factors for the eye may be selected or weighted for priority consideration in the IOL design based on statistical averages for a particular population. In addition, the design of the diffractive element may be adjusted to provide a predetermined visual response within the eye of a subject or patient.

Many of the methods, devices, and systems described herein will take advantage of an optical characteristic of the eye or eye factor. Exemplary eye factors include one or more measurements of the eye (e.g., a pupil diameter at a predetermined viewing condition), a set of pupil diameters each associated with a different predetermined viewing condition, a corneal shape of the anterior corneal surface (e.g., measured by corneal topography and/or by a keratometer), a corneal shape of the posterior corneal surface (e.g., measured by Scheimpflug photography using a Pentacam™ measurement system or the like), a length of the eye (e.g., the axial length of the eye as measured using A-scan biometry, Laser Interference Biometry such as with the IOLMaster™, or the like), an anterior chamber depth, and/or the patient's historic refraction. A wide variety of measurement devices may be used to obtain these or other optical characteristics of the patient's eye useful for the presbyopia mitigation described herein.

Effective presbyopia mitigation for a particular patient may also benefit from data regarding the lifestyle of that patient or lifestyle parameters. Such patient lifestyle parameters may be identified by measurements, observations, questionnaires from the patient or others in contact with or having knowledge about the patient, and the like. The patient lifestyle parameters may be stored in a memory having an updateable database. Exemplary patient lifestyle parameters may include or indicate a preferred reading distance, a preference for reading vision or intermediate vision, an occupation, hobbies, an amount and/or type of outdoor activity, an amount of reading time, an amount of computer time, a work environment, and/or the like. Additionally, one or more of the patient lifestyle parameters may be selected for emphasis (e.g., using a weighting format) when customizing the lens characteristics to the patient.

Based on the eye factors and lifestyle parameters, one or more suitable refractive prescription lenses may be selected and/or designed for a particular presbyopia patient so as to mitigate the disadvantages of presbyopia for that patient. In one embodiment, the prescriptive lens includes a diffractive multifocal lens, and a variety of lens parameters may be determined and/or selected. For example, the diffractive multifocal lens can have one or more echelettes. The term echelette is referred to herein as a generally V-shaped groove formed on the lens surface. Examples of lens parameters include a lens profile height, the diameters associated with the echelettes, the echelette profile shape, and the like. Additionally, the design may, for example, be pupil dependent, and the profile height may vary for each echelette. Each echelette may also have a different diameter. In addition, with pupil dependent designs or other designs emphasizing specific patient desires (e.g. for a patient highly valuing an extended depth of focus), one or more of the echelette diameters may be different from those of more conventional diameters and designs. Furthermore, with pupil dependent designs, the profile shape can be selected to be different for each echelette.

Other lens parameters may also be determined in response to the eye factors or lifestyle parameters, including but not necessarily limited to spectral transmission characteristics, spherical aberration correction, induced negative spherical aberration for mitigation of presbyopia (e.g., U.S. Pat. No. 7,261,412, the disclosure of which is incorporated herein by reference), cylinder (such as a toric multifocal lens), and/or corneal coma correcting optical elements. Cylinder correction and coma correction may also be considered as aberration corrections. Still further variations and alternative lens characteristics and parameters may be included, including biconvex shapes, a diffractive profile(s) on anterior and/or posterior lens surface, etc.

Figure 4:
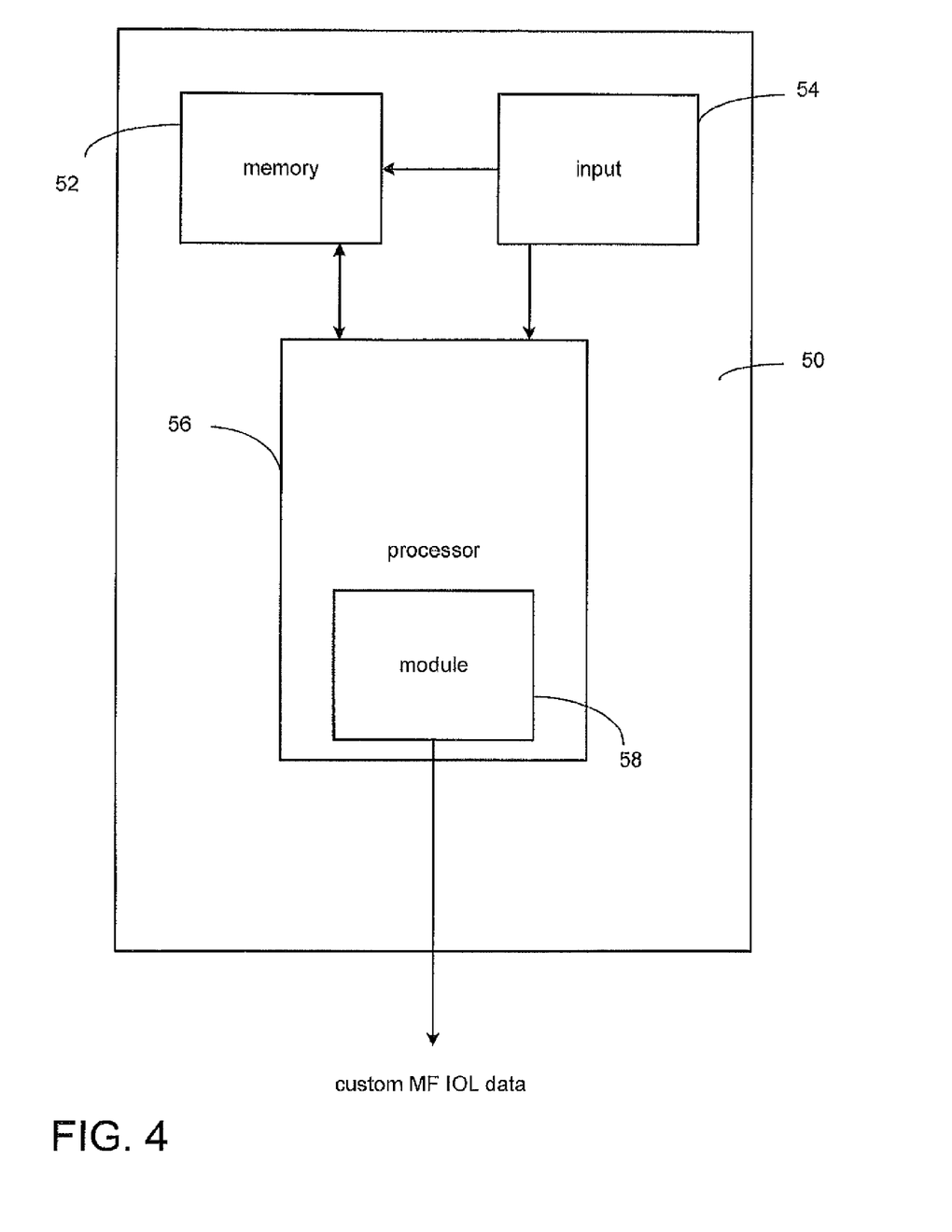
FIG. 4 is a block diagram of an exemplary embodiment of a system for customizing a multifocal lens.

The present invention also provides systems for customizing or optimizing a multifocal IOL for a patient to mitigate presbyopia or other vision conditions of the patient. For example, as shown in FIG. 4, a system 50 can be used for selecting or designing a multifocal IOL. The system 50 includes an input 54 (e.g., a user interface such as a display with an input device (e.g., touch-sensitive screen, mouse, touchpad, keyboard, or the like) that accepts one or more patient lifestyle parameters and one or more eye factors associated with a patient, a memory 52 coupled to the input 54 that stores the patient lifestyle parameters and eye factors, and a processor 56 coupled to the input 54 and the memory 52. The memory 52 may additionally store a database of multifocal IOLs for the patient, which can be populated via the input 54 or by a candidate selection process performed by the processor 56.

The processor 56 includes computer hardware and/or software, often including one or more programmable processor units running machine readable program instructions or code for implementing some or all of one or more of the methods described herein. In one embodiment, the code is embodied in a tangible media such as a memory (optionally a read only memory, a random access memory, a nonvolatile memory, or the like) and/or a recording media (such as a floppy disk, a hard drive, a CD, a DVD, a memory stick, or the like). The code and/or associated data and signals may also be transmitted to or from the processor 56 via a network connection (such as a wireless network, an Ethernet, an internet, an intranet, or the like), and some or all of the code may also be transmitted between components of the system 50 and within the processor 56 via one or more bus, and appropriate standard or proprietary communications cards, connectors, cables, and the like can be included in the processor 56.

The processor 56 is preferably configured to perform the calculations and signal transmission steps described herein at least in part by programming the processor 56 with the software code, which may be written as a single program, a series of separate subroutines or related programs, or the like. The processor 56 may include standard or proprietary digital and/or analog signal processing hardware, software, and/or firmware, and has sufficient processing power to perform the calculations described herein during treatment of the patient. The processor 56 optionally includes a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included with the system 50, and additional processors having a plurality of processing units (or even separate computers) may be employed in a wide range of centralized or distributed data processing architectures.

In this embodiment, the processor 56 determines or selects a particular multifocal IOL based on the patient lifestyle parameters and one or more eye factors. For example, the processor 56 can determine at least one characteristic of the echelettes associated with a candidate multifocal IOL based on the patient lifestyle parameters and the eye factors. A diffractive multifocal IOL can then be selected based on this characteristic(s). One or more of the patient lifestyle parameters and/or eye factors may be weighted by the processor 56 for priority consideration (e.g., to determined the desired characteristic of the candidate multifocal IOL) when selecting or determining the particular multifocal IOL for the patient. In this embodiment, the processor 56 includes a processing module 58 that determines an add power based on the patient lifestyle parameters and one or more eye factors. The module 58 may be a separate processing unit from the processor 56 in other embodiments.

In another embodiment, the system 50 may communicate with a laser system utilizing, for example a laser 60, that directs laser energy onto a surface of the cornea according to a pre-determined ablation profile to reprofile a surface of the cornea. This is particularly useful for combined ophthalmic treatments to effect a desired optical correction. For example, the ablation profile and the determined multifocal IOL characteristics are together considered for mitigating presbyopia associated with the patient's eye or for implementing other optical corrections.

The present invention also provides methods of providing improved ophthalmic lenses. In general, at least one characteristic of the patient's eye is measured, and a multifocal intraocular lens (e.g., a diffractive multifocal intraocular lens) is selected from among a plurality of multifocal intraocular lenses having similar IOL powers based on the measured characteristic of the eye of the patient. At least some of these intraocular lenses have central portions, and selection of the intraocular lens includes selecting between different central portion sizes.

In one embodiment, the method includes determining a set of patient lifestyle parameters for a patient (e.g., by measurements, observations, and questionnaires from the patient or others in contact with or having knowledge about the patient, or the like), determining at least one eye factor for an eye of the patient (e.g., via measurement, retrieved from a database, or the like), determining an add power based on the lifestyle parameter(s) and the eye factor(s), and selecting a multifocal intraocular lens for the patient based on this add power. The eye factors can include an axial length of the eye (e.g., for determining the add power in response to a preferred reading distance and the axial length of the eye), the corneal shape of the eye, the pupil diameter of the eye under a predetermined viewing condition, a set of pupil diameters of the eye under a set of predetermined viewing conditions, a keratometry factor, and/or a corneal radius of curvature factor. Additionally lifestyle parameters include, but are not necessarily limited to, an amount of outdoor activity, an amount of reading time, an amount of computer time, and a work environment.

In another embodiment, based on at least one eye factor, a base power of the multifocal intraocular lens is selected in addition to a separate multifocal lens parameter (e.g., an amount of add power, a depth of focus characteristic, an amount of aberration selected to at least partially correct for an aberration of the cornea of the patient's eye, a spectral transmission characteristic, a pupil dependent add power function) for a multifocal intraocular lens. Additional eye factors include, but are not necessarily limited to, a patient age, a corneal shape, a cataract grade, an estimated postoperative pupil diameter of the eye under predetermined viewing conditions, or a pre-existing intraocular lens.

An exemplary embodiment of a selection of a multifocal intraocular lens includes determining at least one eye factor for an eye of the patient. Based on the at least one eye factor, a base power and/or a multifocal lens parameter is selected for a multifocal intraocular lens. As a more specific example, for many method embodiments, an IOL presbyopia-mitigating add power is determined using a standard or customized near (e.g. reading) viewing distance of the patient. However, the effectiveness of the IOL add power is also determined by the patient's eye dimensions, and primarily by the axial length of the eye. For an eye with an average axial length, a 4 D add may, for example, deliver a near focus at about 33 cm. For an eye with a longer axial length, the desired add power may be larger. For a patient having a substantially standard eye length of about 23.5 mm, with a substantially standard cornea, a 21.7 D IOL base power may be suitable. For this patient, a 4 D add results in a near distance of about 32.1 cm. For an otherwise similar patient with similar corneal characteristics and an eye with an axial length of about 27.5 mm, the anterior chamber depth will typically be larger, and the patient may instead benefit from a base power of about 9.1 D. To have a reading distance of about 32 cm, this other patient may benefit from about a 5.1 D add power for mitigation of myopia. Note that the base power is normally selected based on the axial length of the eye and the corneal curvature (two eye factors).

Exemplary methods for customized mitigation of the presbyopia of a particular patient will also often include determining at least one patient lifestyle parameter of the patient. Based on the at least one lifestyle parameter and the at least one eye factor, a base power and a multifocal lens parameter for a multifocal intraocular lens can then be selected. A more specific example of such embodiments might be a patient who is an active philatelist or stamp collector. Such a patient may, for example, prefer to have a best near vision at a distance of about 20 centimeters. For this patient, an add power of about 5 D might be chosen to achieve the best performance for this patient so as to mitigate their presbyopia for their lifestyle. In contrast, a patient who is an active golfer may wish to instead have a best near vision at a distance of about 1.5 m. An add power of about 1 D could be chosen to achieve an optimal performance for this patient. Patients for whom day and/or night driving or other activities are particularly important, or who would have different lifestyle priorities that may impact their desired visual performance, may similarly have their vision customized (i.e., via the selected multifocal intraocular lens) in response to their lifestyle parameters so as to effectively mitigate the impacts of presbyopia on their lives.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A system (50) for selecting a custom multifocal intraocular lens for a patient, the system comprising:
   a memory (52) storing a first database of lifestyle parameters, a second database of eye factors, and a third database of multifocal intraocular lenses;
   a processor (56) coupled to the memory and configured to:
   determine an add power based on the first database and the second database; and
   select the custom multifocal intraocular lens for the patient from the third database based on the add power;
   wherein the processor is further configured to select a treatment to an eye of the patient subsequent to an insertion of the custom multifocal intraocular lens into the eye, wherein the eye with the custom multifocal intraocular lens has a refraction, and wherein the treatment comprises an adjustment to the refraction comprising a laser assisted refractive ophthalmic surgery.

2. The system of claim 1, wherein the processor is further configured to:
   apply a predetermined weighting to the lifestyle parameters of the first database and the eye factors of the second database to produce a first weighted database of lifestyle parameters and a second weighted database of eye factors; and
   determine the add power based on the first weighted database and the second weighted database.

3. The system of claim 1, wherein at least some of the multifocal intraocular lenses of the third database have a first intraocular lens power, and wherein at least some of the multifocal intraocular lenses of the third database have different optical characteristics, and wherein the custom multifocal intraocular lens is configured to mitigate a presbyopia of the particular patient.

4. The system of claim 1, wherein the first database comprises a preferred reading distance of the patient.

5. The system of claim 4, wherein the second database comprises an axial length of an eye, and wherein the processor is further configured to determine the add power based on the preferred reading distance and the axial length of the eye.

6. The system of claim 1, wherein the second database comprises one or more eye factors selected from a group consisting of a corneal shape of an eye, a pupil diameter of an eye for a predetermined viewing condition, a set of pupil diameters of an eye under a set of predetermined viewing conditions, an axial length of an eye, a keratometry factor, and a corneal radius of curvature factor.

7. The system of claim 1, wherein the custom multifocal intraocular lens has one or more characteristics, and wherein the processor is further configured to select a treatment to the eye comprising an adjustment to at least one of the one or more characteristics of the custom multifocal intraocular lens.

8. The system of claim 1, wherein the processor is further configured to:
  determine a base power based on the second database; and
  select the custom multifocal intraocular lens for the patient from the third database based on the base power.

9. The system of claim 1, wherein the processor is further configured to:
  estimate a pupil size of the patient subsequent to the insertion of the custom multifocal intraocular lens into the eye; and
  select the custom multifocal intraocular lens for the patient from the third database based on the estimated pupil size.

10. The system of claim 9, wherein the custom multifocal intraocular lens has a central portion; and
  the processor is further configured to select a size of the central portion of the custom multifocal intraocular lens based on the estimated pupil size.

11. A system (50) for selecting a custom diffractive multifocal intraocular lens having a diffractive surface with one or more echelettes for a patient, the system comprising:
  a memory (52) storing a first database of lifestyle parameters and a second database of eye factors;
  a processor (58) coupled to the memory and configured to:
    determine at least one characteristic of the one or more echelettes based on the first database and the second database; and
    select the custom diffractive multifocal intraocular lens for the patient based on the at least one characteristic;
  wherein the processor is further configured to select a treatment to an eye of the patient subsequent to an insertion of the custom diffractive multifocal intraocular lens into the eye, wherein the eye with the custom diffractive multifocal intraocular lens has a refraction, and wherein the treatment comprises an adjustment to the refraction comprising a laser assisted refractive ophthalmic surgery.

12. The system of claim 11, wherein the at least one characteristic comprises one or more characteristics selected from a group consisting of one or more heights of the one or more echelettes, one or more diameters of the one or more echelettes, and one or more profile shapes of the one or more echelettes.

13. The system of claim 11, wherein the second database comprises one or more eye factors selected from a group consisting of a corneal shape of an eye, a pupil diameter of the eye for a predetermined viewing condition, an axial length of the eye, a keratometry factor, and a corneal radius of curvature factor.

14. The system of claim 11, wherein the first database comprises a preferred reading distance, wherein the second database comprises an axial length of an eye, and wherein the processor is further configured to determine the at least one characteristic in response to the preferred reading distance and the axial length of the eye.

15. The system of claim 11, wherein the custom diffractive multifocal intraocular lens has one or more characteristics, and wherein the processor is further configured to select a treatment to the eye comprising an adjustment to at least one of the one or more characteristics of the custom diffractive multifocal intraocular lens.

16. A method of selecting a multifocal intraocular lens for a patient, the method comprising the steps of:
  providing a memory storing a first database of one or more lifestyle parameters of the patient, a second database of one or more eye factors of the patient, and a third database of multifocal intraocular lenses;
  determining, with a processor coupled to the memory, a set of different multifocal intraocular lenses from the third database based on first database and the second database, the set of multifocal intraocular lenses having a similar base power; and
  selecting the multifocal intraocular lens for the patient from the set of multifocal intraocular lenses based on the first database and the second database;
  wherein the selecting step further comprises selecting the multifocal intraocular lens based on a treatment to an eye to be performed subsequent to an insertion of the multifocal intraocular lens into the eye, the treatment comprising a laser assisted refractive ophthalmic surgery.

17. The method of claim 16, wherein at least some multifocal intraocular lenses of the set of multifocal intraocular lenses have central portions with associated sizes and add powers, and wherein the step of selecting comprises selecting a first multifocal intraocular lens from the set of multifocal intraocular lenses, the first multifocal intraocular lens has a central portion and an add power both based on the second database.

18. The method of claim 16, further comprising determining an add power of the multifocal intraocular lens for the patient based on the first database and the second database, and wherein the selecting step comprises selecting the multifocal intraocular lens for the patient based on the add power.

19. The method of claim 18, wherein the one or more eye factors of the second database comprise an axial length of the eye, and wherein the step of determining an add power comprises determining the add power based on one or more of eye factors selected from a group consisting of a corneal shape of the eye, a pupil diameter of the eye for a predetermined viewing condition, a keratometry factor, a corneal radius of curvature factor, a preferred reading distance and the axial length of the eye.

20. The method of claim 16, wherein the multifocal intraocular lens for the patient has a diffractive surface with one or more echelettes, wherein the method further comprises determining at least one characteristic of one or more echelettes based on the first database and the second database, and wherein the selecting step comprises selecting the diffractive multifocal intraocular lens from the set of multifocal intraocular lenses based on the at least one characteristic of the one or more echelettes.

21. The method of claim 20, wherein the at least one characteristic comprises one or more characteristics selected from a group consisting of one or more heights of the one or more echelettes, one or more diameters of the one or more echelettes, and one or more profile shapes of the one or more echelettes.

22. The method of claim 16, wherein the selecting step comprises selecting one or more multifocal lens parameters for the multifocal intraocular lens based on the first database and the second database.

23. The method of claim 22, wherein the one or more multifocal lens parameters comprises one or more parameters selected from a group consisting of an add power amount, a depth of focus characteristic, an aberration amount selected to at least partially correct for an aberration of the cornea of the eye, a spectral transmission characteristic, and a pupil dependent add power function.

24. The method of claim 22, wherein the one or more eye factors of the second database comprise one or more factors selected from a group consisting of a patient age, a corneal shape, a cataract grade, an estimated postoperative pupil diameter of the eye for a predetermined viewing condition, and a pre-existing intraocular lens.

25. The method of claim 22, wherein the one or more lifestyle parameters of the first database comprise one or more parameters selected from a group consisting of an amount of outdoor activity, an amount of reading time, an amount of computer time, and a work environment.

26. The method of claim 16, wherein the multifocal intraocular lens has one or more characteristics, and wherein the selecting step further comprises selecting the multifocal intraocular lens based on the second database and a treatment to an eye subsequent to an insertion of the multifocal intraocular lens into the eye, the treatment comprising an adjustment to at least one of the one or more characteristics of the multifocal intraocular lens.

\* \* \* \* \*